(12) United States Patent
Takai et al.

(10) Patent No.: US 8,420,064 B2
(45) Date of Patent: Apr. 16, 2013

(54) HAIR-TREATING AGENT AND METHODS OF TREATING HAIR

(75) Inventors: Masanori Takai, Wakayama (JP);
Tadanori Yoshimura, Wakayama (JP);
Kazuhisa Fukuhara, Sumida-ku (JP);
Takao Shinozaki, Sumida-ku (JP)

(73) Assignee: Kao Corporation, Tokyo (JP)

( * ) Notice: Subject to any disclaimer, the term of this patent is extended or adjusted under 35 U.S.C. 154(b) by 136 days.

(21) Appl. No.: 12/819,752

(22) Filed: Jun. 21, 2010

(65) Prior Publication Data

US 2010/0254930 A1 Oct. 7, 2010

Related U.S. Application Data

(62) Division of application No. 11/578,146, filed as application No. PCT/JP2005/006775 on Apr. 6, 2005, now abandoned.

(30) Foreign Application Priority Data

| Apr. 7, 2004 | (JP) | 2004-113077 |
| Oct. 8, 2004 | (JP) | 2004-296185 |
| Dec. 8, 2004 | (JP) | 2004-355309 |
| Dec. 28, 2004 | (JP) | 2004-379418 |

(51) Int. Cl.
*A61K 8/89* (2006.01)

(52) U.S. Cl.
USPC ..................................... 424/70.12

(58) Field of Classification Search .................. None
See application file for complete search history.

(56) References Cited

U.S. PATENT DOCUMENTS

| 2,782,790 A | 2/1957 | Hersh et al. |
| 3,472,243 A | 10/1969 | Wall et al. |
| 4,175,572 A | 11/1979 | Hsiung et al. |
| 4,372,977 A | 2/1983 | Lover et al. |
| 4,708,743 A | 11/1987 | Schmidt |
| 4,986,983 A * | 1/1991 | Gerstein ............ 424/70.21 |
| 5,661,215 A | 8/1997 | Gee et al. |
| 6,214,927 B1 | 4/2001 | Craig et al. |
| 6,953,584 B1 | 10/2005 | Samain et al. |
| 2003/0185779 A1 | 10/2003 | Mitsumatsu et al. |
| 2006/0110351 A1 | 5/2006 | Koehler et al. |

FOREIGN PATENT DOCUMENTS

| EP | 0 159 628 A2 | 10/1985 |
| EP | 0 460 683 A2 | 12/1991 |
| EP | 0 460 683 A3 | 12/1991 |
| EP | 1 069 149 A1 | 1/2001 |
| JP | 36-21172 | 11/1961 |
| JP | 36 21172 | 11/1961 |
| JP | 61000007 | 1/1986 |
| JP | 61 129186 | 6/1986 |
| JP | 2 160836 | 6/1990 |
| JP | 4-270209 | 9/1992 |
| JP | 6-263875 | 9/1994 |
| JP | 2000 510167 | 8/2000 |
| JP | 2001-2989 | 1/2001 |
| JP | 2001-181572 | 7/2001 |
| JP | 2001 513824 | 9/2001 |
| JP | 2002 097114 | 4/2002 |
| JP | 2003-510261 | 3/2003 |
| WO | 01 15658 | 3/2001 |
| WO | WO 2004/012691 A1 | 2/2004 |

OTHER PUBLICATIONS

English Translation of JP36021172.*
English Abstract of JP2-59509, retrieved from East.*
English Translation of JP36021172, 1961.*
English Abstract of JP2-59509, retrieved from East, 1990.*
Supplementary European Search Report Issued Jan. 27, 2012, in European Patent Application No. 05728472.1.

\* cited by examiner

*Primary Examiner* — Blessing Fubara
*Assistant Examiner* — Jennifer Berrios
(74) *Attorney, Agent, or Firm* — Oblon, Spivak, McClelland, Maier & Neustadt, L.L.P.

(57) ABSTRACT

A hair processing composition contains an alkoxysilane (1); an organic acid; and water and has a pH in a range of from 2 to 5.
A method for processing hair includes mixing while stirring the above-described hair processing composition and allowing a silanol compound (2) produced through hydrolysis of the alkoxysilane (1) represented by general formula (1) to penetrate into the hair.
A method for processing hair further includes applying to hair an acidic aqueous solution or an alkaline aqueous solution after the silanol compound (2) has penetrated into the hair to accelerate the polymerization of the silanol compound.

$$R^1_p Si(OR^2)_{4-p} \quad (1)$$

$$R^1_p Si(OH)_n (OR^2)_{4-p-n} \quad (2)$$

wherein $R^1$ and $R^2$ represent a $C_1$-$C_6$ alkyl group or a $C_2$-$C_6$ alkenyl group, p represents an integer of from 0 to 3, and n represents an integer of not less than 1 and not more than (4-p).

21 Claims, 3 Drawing Sheets

HAIR-TREATING AGENT AND METHODS OF TREATING HAIR

FIELD OF THE INVENTION

This invention relates to a hair processing composition which imparts strength/body to hair and a method for processing hair.

BACKGROUND OF THE INVENTION

As a method for improving physical properties, appearance and feeling of hair by making hair-component materials penetrate inside of the hair, it has hitherto been proposed to supplement the hair with decomposed matters and derivatives of hair such as collagen, keratin or the like which are similar to the components of hair. However, such method has failed to obtain satisfactory effects.

On the other hand, there has been known a technique for strengthening hair by using an alkyltrialkoxysilane for the hair treated with an alkali (for example, refer to JP-A-61-7). Also proposed is a method for protecting and strengthening keratin substances in nails, hair or the like by applying thereto an organic silicon compound obtained by partially or totally hydrolyzing an organic silicon compound or the like and polymerizing the resulting hydrolysate (for example, refer to JP-A-2000-510167 and JP-A-2002-97114).

However, such techniques have the problems that the organic silicon compound loses its effect upon washing and that the feeling of the surface of keratin becomes different from its inherent feeling since the compound exists only on the surface of keratin.

DISCLOSURE OF THE INVENTION

The present invention provides a hair processing composition comprising an alkoxysilane represented by the following formula (1):

$$R^1_p Si(OR^2)_{4-p} \quad (1)$$

wherein $R^1$ and $R^2$ represent a straight or branched alkyl group having 1 to 6 carbon atoms or a straight or branched alkenyl group having 2 to 6 carbon atoms, p "$R^1$"(s) (i.e. $R^1$(s) appearing p times) and (4−p) "$R^2$"(s) (i.e. $R^2$(s) appearing (4−p) times) may be the same or different, and p represents an integer of 0 to 3; an organic acid and water, said composition having a pH in a range of 2 to 5.

Also the present invention provides a method for processing hair which comprises mixing while stirring the above-mentioned hair processing composition, and applying the composition to hair to allow a silanol compound represented by the following general formula (2):

$$R^1_p Si(OH)_n (OR^2)_{4-p-n} \quad (2)$$

wherein $R^1$, $R^2$ and p represent the same meaning as in the above, n represents an integer not less than 1 and not more than (4−p), and p "$R^1$"(s) and (4−p−n) "$R^2$"(s) may be the same or different, which is produced by the hydrolysis of the alkoxysilane represented by general formula (1), to penetrate into the hair.

Further, the present invention provides a method for processing hair which comprises mixing while stirring a hair processing composition ($A_1$) which contains the alkoxysilane of general formula (1), an organic acid and water as constituents, applying to hair a hair processing composition ($A_2$) which is produced after the alkoxysilane is hydrolyzed and converted to a silanol compound represented by the general formula (2), and then applying as a polymerization accelerator an acidic aqueous solution ($B_a$) which, when mixed with the hair processing composition ($A_2$) at a weight ratio of 1:1, makes the pH of the hair processing composition ($A_2$) in a range of from 1 to 4, or an alkaline aqueous solution ($B_b$) which, when added to the hair processing composition ($A_2$) at a weight ratio of 1:1, makes the pH of the hair processing composition ($A_2$) in a range of from 8 to 12.

Furthermore, the present invention provides a hair reforming composition which includes the following hair processing composition (A) and the following acidic aqueous solution ($B_a$), or the following hair processing composition (A) and the following alkaline aqueous solution ($B_b$): (A) a hair processing composition containing the alkoxysilane of formula (1), an organic acid having a first dissociation index (pKa1) in a range of from 4.1 to 5, and water, ($B_a$) a polymerization accelerator which contains an organic or inorganic acid having a first dissociation index (pKa1) less than 4.1 and which, when mixed with the hair processing composition (A) at a weight ratio of 1:1, makes the pH of the hair processing composition (A) in a range of from 1 to 4, ($B_b$) a polymerization accelerator which, when mixed with the hair processing composition (A) at a weight ratio of 1:1, makes the pH of the hair processing composition (A) in a range of from 8 to 12.

MODES FOR CARRYING OUT THE INVENTION

Figure 1:
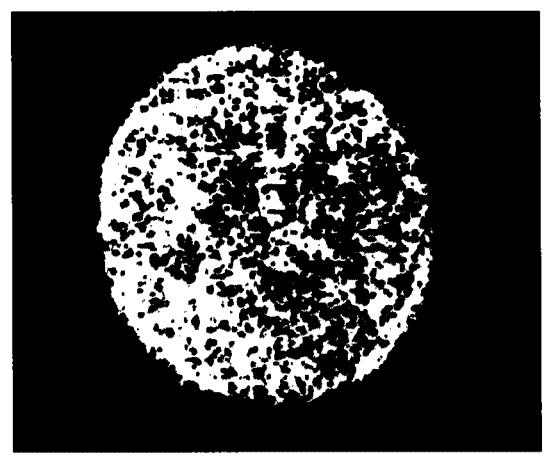
FIG. 1 is an FE-SEM-EDS elemental silicon mapping of the cross-section of the hair after subjecting to the process of Example 1.

This invention relates to a hair processing composition which can impart excellent strength/body to hair fibers, particularly hair not having strength/body (hair which is damaged by chemical treatment or the like, thin hair of westerners or elderly people, or the like) and a method for processing hair. The term "impart strength/body" herein means enhancing the elasticity or flexibility of hair.

The present inventors have found that by the co-existence of an organic acid in the hydrolysis of an alkoxysilane, it is possible to control moderately the polymerization rate of the silanol compounds produced by the hydrolysis and as a consequence allow the silanol compounds to penetrate into hair and polymerize inside the hair, thereby imparting excellent strength/body to the hair. Namely, the silanol compounds represented by general formula (2) are inherently unstable and thus the molecules thereof are readily dehydrated and condensed with one another to give large molecules, whereby failing to penetrate into the hair. According to the present invention, it is possible to stabilize the silanol compounds as monomolecules or lower molecules such as dimmers or trimmers at the largest, whereby enabling efficient penetration of the silanol compounds into the inside of hair. In addition, the present inventors have found that by applying an acidic aqueous solution or an alkaline aqueous solution after penetration of the silanol compounds into hair, it is possible to accelerate polymerization of the silanol compounds and largely reduce the time required for the polymerization.

According to the present invention, it is possible to reform hair from the inside of the hair by allowing silanol compounds produced through hydrolysis of an alkoxysilane to penetrate into the hair and polymerize inside the hair. Therefore the present invention is apparently superior in hair reforming effects, feeling and durability compared to the conventional techniques in which an organic silicon compound is used to form a coating on the surface of hair to strengthen and protect the hair. According to the method for processing hair of the present invention, the diameter of the hair is increased and excellent strength/body are imparted particularly to hair not having strength/body (damaged hair, thin hair or the like). In addition, manageability-enhancing effects and unduly hair-curing effects are obtainable. These effects are kept even when shampooing is repeated.

I. Hair Processing Composition Comprising a Silanol Compound

[Alkoxysilane (1)]

In $R^1$ and $R^2$ in general formula (1), examples of the alkyl group include methyl group, ethyl group, propyl group, butyl group, isopropyl group, isobutyl group, and t-butyl group, and examples of the alkenyl group include vinyl group and allyl group. $R^2$ is preferably ethyl in view of the safety of the by-products of the hydrolysis and the reactivity of the hydrolysis reaction.

When the hair processing composition according to the present invention is of a two agent type, an alkoxysilane (1) is added to a first agent which does not contain water, and after mixing with a second agent which contains water, it is converted to a water-soluble silanol compound (2) through hydrolysis, whereby penetration into hair is enabled. In view of the physical properties of the silanol compound (2) produced and penetration thereof into hair, p in general formula (1) is preferably 0 to 2. Examples of the alkoxysilane (1) include $C_{1-6}$alkyltrimethoxysilanes, $C_{1-6}$alkyltriethoxysilanes, and di-$C_{1-6}$alkyldiethoxysilanes.

The content of the alkoxysilane (1) is, in view of the reactivity of a cross-linking reaction, preferably not less than 4% by weight of the hair processing composition according to the present invention (the total amount of the first agent and the second agent when the hair processing composition is of a two agent type; hereinafter, this is also applicable), more preferably not less than 12% by weight, and is preferably not more than 82% by weight, more preferably not more than 58% by weight. In addition, when the hair processing composition is of a two agent type, the content of the alkoxysilane (1) in the first agent is preferably in a range of 70 to 100% by weight, more preferably 80 to 100% by weight, even more preferably 90 to 100% by weight in view of storage stability.

(Organic Acid)

Examples of the organic acids include oxalic acid (pKa=1.04, 3.82), maleic acid (pKa=1.75, 5.83), aspartic acid (pKa=1.93, 3.70), salicylic acid (pKa=2.81), tartaric acid (pKa=2.82, 3.96), fumaric acid (pKa=2.85, 4.10), citric acid (pKa=2.90, 4.34), malic acid (pKa=3.24, 4.71), succinic acid (pKa=4.00, 5.24), formic acid (pKa=3.55), lactic acid (pKa=3.66), glutaric acid (pKa=4.13, 5.01), adipic acid (pKa=4.26, 5.03), acetic acid (pKa=4.56) and propionic acid (pKa=4.67). However, in view of easiness in pH regulation, the organic acid is preferably one having a first dissociation index (pKa1) in a range of from 1.9 to 5.0, more preferably 2.9 to 5.0, even more preferably 3.5 to 5.0. Among them, glutaric acid, adipic acid, acetic acid and propionic acid which are easy to control the polymerization reaction of the silanol compounds (2) are preferred, and adipic acid which is low in odor is more preferred.

When the hair processing composition according to the present invention is of a two agent type, it is preferable to add the organic acid to the second agent separately from the alkoxysilane which is added to the first agent from the viewpoint of solubility and storage stability. The content of the organic acid is preferably in a range of from 0.001 to 5% by weight, more preferably 0.001 to 1% by weight of the hair processing composition of the present invention from the viewpoint of suppression of the polymerization reaction.

[Water]

When the hair processing composition according to the present invention is of a two agent type, water is added to the second agent separately from the alkoxysilane which is added to the first agent, and the content thereof is preferably in a range of from 20 to 95% by weight, more preferably 30 to 86% by weight of the hair processing composition of the present invention from the viewpoint of sufficiently swelling hair and allowing sufficient penetration of the silanol compound (2) produced through hydrolysis into hair.

[Surfactant]

The hair processing composition of the present invention may contain additionally a surfactant in order to conduct the processing operation more conveniently with a certainty in a short time. By the co-existence of a surfactant in the hair processing composition, hydrolysis of the alkoxysilane can be promoted and the mixing operation during hydrolysis can be simplified. In addition, certainty of the processing is enhanced since the appearance of the system is changed from being white turbid to clear and thus the progress of the hydrolysis can be readily confirmed. When the hair processing composition of the present invention is of a two agent type, the surfactant may be added to either the first agent or the second agent or to both agents, but is preferably added at least to the second agent, provided that the surfactant may be added to the first agent when the first agent does not contain water. As the surfactant, any of nonionic surfactants, anionic surfactants, cationic surfactants and amphoteric surfactants may be used.

Examples of the nonionic surfactants include polyoxyalkylene alkyl ethers, polyoxyalkylene alkenyl ethers, higher fatty acid sucrose esters, polyglyceryl fatty acid esters, higher fatty acid mono- or di-ethanol amides, polyoxyethylene hydrogenated castor oils, polyoxyethylene sorbitan fatty acid esters, polyoxyethylene sorbitol fatty acid esters, alkyl saccharide surfactants, alkylamine oxides, and alkylamide amine oxides. Among them, polyoxyalkylene alkyl ethers and polyoxyethylene hydrogenated castor oils are preferred and polyoxyethylene alkyl ethers are more preferred.

Examples of the anionic surfactants include alkylbenzene sulfonate salts, alkyl or alkenyl ether sulfate salts, alkyl or alkenyl sulfate salts, olefin sulfonate salts, alkane sulfonate salts, saturated or unsaturated fatty acid salts, alkyl or alkenyl ether carboxylate salts, α-sulfone fatty acid salts, N-acylamino acid surfactants, phosphate mono- or di-ester surfactants, and sulfosuccinate esters. Examples of the counter ions of the anionic residues of the above-mentioned surfactants include alkali metal ions such as sodium ion and potassium ion; alkaline earth metal ions such as calcium ion and magnesium ion; ammonium ion; and alkanolamines having 1 to 3 alkanol groups of 2 to 3 carbon atoms (e.g. monoethanolamine, diethanolamine, triethanolamine or triisopropanolamine). Examples of the counter ions of the cationic residues include halide ions such as chloride ion, bromide ion and iodide ion; methosulfate ion, and succharinate ion.

Examples of the cationic surfactants include quaternary ammonium salts represented by the following formula (3):

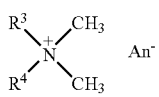

(3)

wherein, $R^3$ and $R^4$ each independently denote a hydrogen atom, an alkyl group having 1 to 28 carbon atoms or a benzyl group, excluding the case where they are simultaneously a hydrogen atom or a benzyl group or they are a lower alkyl group having 1 to 3 carbon atoms, and $An^-$ denotes an anion.

In formula (3), one of $R^3$ and $R^4$ is preferably an alkyl group having 16 to 24 carbon atoms, more preferably an alkyl group having 22 carbon atoms, even more preferably a straight alkyl group, and the other is preferably a lower alkyl group having 1 to 3 carbon atoms, more preferably a methyl group. Examples of the anion $An^-$ include halide ions such as a chloride ion and bromide ion; and organic anions such as an ethyl sulfate ion and methyl carbonate ion. Halide ions are preferred and chloride ion is more preferred.

As the cationic surfactants, preferred are mono long-chain alkyl quaternary ammonium salts, specifically cetyltrimethylammonium chloride, stearyltrimethylammonium chloride, arachyltrimethylammonium chloride and behenyltrimethylammonium chloride. Among them, preferred are stearyltrimethylammonium chloride and behenyltrimethylammonium chloride.

Examples of the amphoteric surfactants include imidazoline-type, carbobetaine-type, amidobetaine-type, sulfobetaine-type, hydroxysulfobetaine-type and amidosulfobetaine-type surfactants.

Among them, from the viewpoint of the emulsification ability (miscibility of an alkoxysilane (1), an organic acid, water and a surfactant), preferred are nonionic surfactants having an HLB in a range of 9 to 15, more preferably 11 to 14. Incidentally, the HLB herein denotes a value calculated from Griffin method.

The surfactant may be used in combination of two or more thereof and the content thereof is preferably 0.1 to 20% by weight, more preferably 0.5 to 15% by weight, even more preferably 1 to 10% by weight of the hair processing composition of the invention in view of promotion of emulsification and hydrolysis during mixing.

[pH]

In the hair processing composition of the invention, it is necessary to retard the polymerization reaction in order to hydrolyze an alkoxysilane (1) to produce a silanol compound (2), allow the silanol compound (2) to penetrate into the hair and cause a polymerization reaction in the hair. For this purpose, the pH (20° C.) is adjusted to 2 to 5, preferably 3 to 4. Incidentally, in the case of a two-agent type composition, the pH (20° C.) of the second agent is adjusted to the above-mentioned range.

[Other Components]

For the purposes of dissolving a silanol compound (2) and promoting penetration of the silanol compound into hair, it is possible to use a water-soluble organic solvent such as a monovalent lower alcohol having 1 to 4 carbon atoms, e.g. methanol or ethanol, a multivalent alcohol, e.g. glycerol or propylene glycol, an amide, e.g. formaldehyde, N,N-dimethylformamide or N-methylpyrrolidone, a sulfoxide, e.g. dimethylsulfoxide, a sulfone, e.g. sulforan, a phosphate ester, e.g. trimethyl phosphate, an alcohol ethoxylate, e.g. ethoxyethyl alcohol, an ether, e.g. polyethylene glycol, tetrahydrofuran or 1,2-diethoxyethane, or a ketone, e.g. acetone or methylethylketone. However, if the amount of the solvent is too much, hair does not sufficiently swell upon application of the hair processing composition of the invention to hair, whereby the silanol compound (2) hardly penetrates into the hair sufficiently. Thus, the amount of the water-soluble organic solvent used is preferably not more than 35% by weight, more preferably not more than 20% by weight of the hair processing composition of the invention. In addition thereto, the hair processing composition of the invention after hydrolysis of the alkoxysilane (1) contains $R^2OH$ as a by-product.

The hair processing composition of the invention may be optionally incorporated with other components such as pH adjusters, oleums, silicone derivatives, cationic polymers, humectants, viscosity controlling agents, fragrances, dyes, ultraviolet absorbers, antioxidants, antibacterial agents and antiseptics, depending upon the purpose of use.

[Form of Hair Processing Composition]

The hair processing composition of the present invention is preferably in the form of a two agent-type composition having a first agent comprising an alkoxysilane (1) and a second agent comprising an organic acid and water and having a pH of 2 to 5 from the viewpoint of ensuring a long term stability, but may be one prepared by mixing an alkoxysilane (1), an organic acid and water, as well as a surfactant and other optional components immediately before use and adjusting the pH to 2 to 5.

When the hair processing composition of the present invention is a two agent-type composition, a surfactant is preferably included in the second agent, but may be included in the first agent if the first agent does not contain water. The other optional components are preferably included in the second agent, but may be included in the first agent if they are non-aqueous liquid components or solid components.

When the hair processing composition of the present invention is prepared by mixing an alkoxysilane (1), an organic acid and water, as well as a surfactant and other optional components immediately before use, the order of mixing is not particularly restricted. However, since a silanol compound (2) produced through hydrolysis immediately initiates a polymerization reaction, it is preferable to add the alkoxysilane (1) after mixing an organic acid and water to suppress the polymerization reaction. When a thickening agent is added as the other components, the thickening agent is preferably added after hydrolysis of the alkoxysilane (1) since a thickened solution decreases the rate of the hydrolysis.

By mixing the first agent and the second agent immediately before use when the hair processing composition of the present invention is a two agent type composition, or by mixing an alkoxysilane (1), an organic acid and water, as well as, if necessary, a surfactant and other optional components when the composition is prepared upon demand, the alkoxysilane (1) is converted to a water-soluble silanol compound (2) through hydrolysis, thereby enabling penetration thereof into hair. From the view point of the physical properties of the silanol compound (2) and penetration thereof into hair, p is preferably 0 to 2, n is preferably 2 to 4, and (4−p−n) is preferably 0 in general formula (2). The molecular weight of the silanol compound (2) is preferably 300 or less, more preferably from 90 to 200 in view of easiness of penetration into hair.

[Hair Processing Method]

For processing hair with the hair processing composition of the invention, it is preferable to mix the first agent and the second agent immediately before use when the hair processing composition is a two agent-type composition, or mix an alkoxysilane (1), an organic acid and water, as well as, if necessary, a surfactant and other optional components immediately before use when the hair processing composition is prepared upon demand, then mix the resulting mixture while stirring by means of shaking or the like, and, after visually confirming that the mixed solution has one uniform phase, apply the resulting mixture to hair. When a surfactant is included, the stirring operation after mixing can be facilitated. When a surfactant is not included, it is preferable to continuously stir until one uniform phase is obtained, while usually initial one time stirring or stirring once per several minutes is sufficient when a surfactant is included. The mixing ratio of the first agent to the second agent (weight ratio of first agent/second agent) is preferably in a range of from 80/20 to 1/99, more preferably 60/40 to 20/80. Although the two agents are not soluble with each other immediately after mixing, the mixture becomes to have one uniform phase, whereby it is possible to confirm that the alkoxysilane (1) has been hydrolyzed to produce a silanol compound (2). Particularly when a surfactant is included, the mixture is in a white turbid emulsified state or partially emulsified state immediately after mixing. However, upon allowing to stand or, if necessary, continuous stirring, the mixture turns to a clear mixture, whereby generation of a silanol compound (2) can be readily confirmed.

By allowing the resulting mixture to stand, the polymerization reaction of the silanol compound (2) proceeds. Thus, the resulting mixture is applied preferably within 30 minutes, more preferably within 15 minutes, whereby the silanol compound (2) can penetrate into hair. The hair to be applied may be wet or dry. It is preferable to apply the mixture in an amount of 0.5 to 3 g per 1 gram of dry hair. The subject to be applied may be hair of the head of a human or hair of a wig or the like.

In order to allow sufficient penetration of the silanol compound (2) into hair, the period of time for retaining the hair applied with the hair processing composition is preferably 15 to 90 minutes, more preferably 20 to 60 minutes. By allowing the hair to stand for a predetermined time after application, the silanol compound (2) penetrates into the inside of hair. During this period, the part of the hair applied with the composition may be heated to 40 to 90° C., preferably 40 to 60° C. After the silanol compound (2) has sufficiently penetrated into the hair, the excess amount of the hair processing composition is removed by a towel or the like, if necessary, and then the hair may be dried by hot air or applied with an acid or a base to promote the polymerization reaction of the silanol compound inside the hair. It is preferable to finally remove sufficiently the silanol compound adhered to the surface of the hair or polymerized products thereof after the polymerization reaction by shampooing or the like because they may form a film after drying of the hair and cause deterioration of the feeling of hair.

II. Concomitant Use of Polymerization Accelerator

In the following, a case where a polymerization accelerator is used in combination with the hair processing composition comprising the silanol compound is described.

The term "hair processing composition ($A_1$)" described below refers to a hair processing composition before the hydrolysis of an alkoxysilane (1). The term "hair processing composition ($A_2$)" refers to a hair processing composition after the alkoxysilane (1) is converted to a silanol compound (2) through hydrolysis. The term "hair processing composition (A)" or merely "hair processing composition" includes both the "hair processing composition ($A_1$)" and the "hair processing composition ($A_2$)". The term "polymerization accelerator ($B_a$)" refers to a polymerization accelerator in which an acidic aqueous solution is used as a polymerization accelerator, and the term "polymerization accelerator ($B_b$)" refers to a polymerization accelerator in which an alkaline aqueous solution is used as a polymerization accelerator. The term "polymerization accelerator" includes both the "polymerization accelerator ($B_a$)" and the "polymerization accelerator ($B_b$)".

<<Hair Processing Composition>>

The first step of a method for processing hair concomitantly using the polymerization accelerator includes mixing while stirring a hair processing composition ($A_1$) comprising an alkoxysilane (1), an organic acid and water as constituents as mentioned above, and applying to hair a hair processing composition ($A_2$) which is produced after the alkoxysilane is hydrolyzed and converted to a silanol compound (2) so that it penetrates into the hair.

The components incorporated, the amount of each component, the pH and the form of the hair processing composition used herein are fundamentally approximately similar to those in the case where the above-mentioned polymerization accelerator is not concomitantly used. Namely, the preferred compounds among the alkoxysilanes (1), the content each of the alkoxysilane (1), organic acid and water, water-soluble organic solvents and other optional components, and preferred form of the hair processing composition are similar to those in the case where the above-mentioned polymerization accelerator is not concomitantly used. The pH (20° C.) of hair processing composition ($A_2$) is adjusted preferably to 2 to 5, more preferably 3 to 4.

As the organic acid, preferred are those having a first dissociation index (pKa1) in a range of from 4.1 to 5.0, more preferably 4.1 to 4.7 in view of sufficiently suppressing the polymerization of the silanol compound (2) to allow sufficient penetration thereof into hair and easiness in pH adjustment. Specifically, examples thereof include glutaric acid (pKa=4.13, 5.01), adipic acid (pKa=4.26, 5.03), acetic acid (pKa=4.56) and propionic acid (pKa=4.67). Among them, adipic acid is preferred because it facilitates control of the polymerization reaction of the silanol compound (2) and has less odor.

<<Polymerization Accelerator>>

The second step of a method for processing hair concomitantly using the polymerization accelerator includes applying an acidic aqueous solution ($B_a$) or an alkaline aqueous solution ($B_b$) used as a polymerization accelerator to hair after the silanol compound has penetrated into the hair in order to promote polymerization of the silanol compound. Particularly when the organic acid included in the hair processing composition has a pKa in a range of from 4.1 to 5, the silanol compound penetrated into the hair becomes stable and hardly polymerizes. Thus concomitant use of the polymerization accelerator for polymerization is effective for enhancing the effect and reducing the time.

[Acidic Aqueous Solution ($B_a$)]

When an acidic aqueous solution ($B_a$) is used, namely, when an acidic aqueous solution is used for promotion of the polymerization of the silanol compound which has penetrated into hair, the acid is preferably such an acid having a pKa less than 4.1, more preferably 3.7 or less in view of the reaction rate of the polycondensation. Incidentally, the pKa herein means a first dissociation constant (pKa1) when the acid is di- or higher acid. Among them, examples of the organic acids include oxalic acid (pKa=1.04, 3.82), maleic acid (pKa=1.75, 5.83), aspartic acid (pKa=1.93, 3.70), salicylic acid (pKa=2.81), tartaric acid (pKa=2.82, 3.96), fumaric acid (pKa=2.85, 4.10), citric acid (pKa=2.90, 4.34), malic acid (pKa=3.24, 4.71), succinic acid (pKa=4.00, 5.24), formic acid (pKa=3.55) and lactic acid (pKa=3.66), and examples of the inorganic acids include phosphoric acid (pKa=2.15) and hydrochloric acid (pKa=−8). Among them, malic acid, lactic acid, hydrochloric acid and phosphoric acid are preferred.

As the acidic aqueous solution ($B_a$), such solution which, when mixed with a hair processing agent (A) (preferably a hair processing agent ($A_2$)) at a weight ratio of 1:1, makes the pH of the hair processing agent (A) in a range of from 1 to 4, preferably 1.5 to 3.5, more preferably 2 to 3.3 is used in view of the reaction rate of the polycondensation. The acidic aqueous solution ($B_a$) may be a buffer type solution providing the above-described pH range.

[Alkaline Aqueous Solution ($B_b$)]

When an alkaline aqueous solution ($B_b$) is used, namely, when an alkaline aqueous solution is used for promotion of the polymerization of the silanol compound which has penetrated into hair, it is possible to use as the alkali carbonates such as sodium carbonate and potassium carbonate; hydroxides such as sodium hydroxide and potassium hydroxide; and alkanolamines such as monoethanolamine and 2-amino-2-methyl-1-propanol. As the alkaline aqueous solution ($B_b$), such solution which, when mixed with a hair processing agent (A) (preferably a hair processing agent ($A_2$)) at a weight ratio of 1:1, makes the pH of the hair processing agent in a range of from 8 to 12.0, preferably 8.5 to 12, more preferably 9 to 10 is used in view of the reaction rate of the polycondensation.

[Other Components]

The polymerization accelerator may be optionally incorporated with other components such as surfactants, oleums, silicone derivatives, cationic polymers, humectants, viscosity controlling agents, fragrances, dyes, ultraviolet absorbers, antioxidants, antibacterial agents and antiseptics depending upon the purpose of use. It may be converted to an emulsion by using an oleum and a surfactant.

<<Hair Processing Method>>

Processing of hair with the hair processing composition, namely the first step of a method for processing hair concomitantly using the polymerization accelerator, is preferably conducted by mixing the first agent and the second agent immediately before use when the hair processing composition is a two agent-type composition, or mixing the alkoxysilane (1), the organic acid and water, as well as other optional components immediately before use when the hair processing composition is prepared upon demand, then stirring the resulting mixture by means of shaking, and, after visually confirming that the mixed solution has one uniform phase, applying the resulting mixture, i.e. a hair processing composition ($A_2$), to hair. If the composition is of one agent type, the mixing ratio of the first agent to the second agent (weight ratio of the first agent/second agent) is preferably in a range of from 80/20 to 1/99, more preferably 60/40 to 20/80. Although these agents are not soluble with each other immediately after mixing, the mixture turns to having one uniform phase while continuously stirring by shaking, whereby it is possible to confirm that the alkoxysilane (1) has been hydrolyzed to produce a silanol compound (2).

By allowing the hair processing agent ($A_2$) to stand, the polymerization reaction of the silanol compound (2) proceeds. Thus, the resulting hair processing agent ($A_2$) is applied preferably within 30 minutes, more preferably within 15 minutes, whereby the silanol compound (2) can penetrate into the hair. The hair to be applied may be wet or dry. It is preferable to apply the hair processing agent ($A_2$) in an amount of 0.5 g to 3 g per 1 gram of dry hair. The subject to be applied may be hair of the head of a human or hair of a wig or the like.

In order to allow sufficient penetration of the silanol compound (2) into hair, the period of time for retaining the hair applied with the hair processing composition ($A_2$) is preferably 10 to 90 minutes, more preferably 20 to 60 minutes. By allowing the hair to stand for a predetermined time after application, penetration and polymerization reaction of the silanol compound (2) proceed. During this period, the hair may be wrapped with a wrapping or the like to avoid drying of the hair, or the part of the hair applied with the composition may be heated to 40 to 90° C., preferably 40 to 60° C.

After treatment with the hair processing composition ($A_2$), a polymerization accelerator may be applied to the hair as it is. However, it is preferable to apply the polymerization accelerator after removing the hair processing composition adhered to the surface of the hair with a towel or the like to avoid unnecessary dilution of the polymerization accelerator.

After application of the polymerization accelerator, the time of leaving the hair to stand for promoting the polymerization of the silanol compound (2) is preferably 1 to 60 minutes, more preferably 10 to 30 minutes. During this period, the hair may be wrapped with a wrapping or the like to avoid drying of the hair, or the part of the hair applied with the composition may be heated to 40 to 90° C., preferably 40 to 60° C. Thereafter, the hair may be washed by shampooing or the like and optionally dried.

EXAMPLES

Test Example 1

Time Required for Polymerization of Silanol Compound

In a 300 mL eggplant-shaped flask, 74.9 g of ion-exchange water was weighed and placed, and 0.1 g each of the additives (an organic acid, an inorganic acid or an alkali agent) shown in Table 1 was added thereto. The resulting mixture was stirred at room temperature to dissolve the additives and was mixed with 25.0 g of methyltriethoxysilane. The resulting mixture was stirred in a thermostatic tank kept at 40° C. using a stirring bar equipped with stirring blades having a half-moon shape of 7 cm and made of Teflon (registered trademark) at a stirring rate of 200 rpm. Upon allowing to stand, the mixture initially separated into two phases but turned into a clear uniform aqueous solution (containing methylsilanetriol, ethanol and water) after completion of a reaction because the methylsilanetriol produced through a hydrolysis reaction is water-soluble. Incidentally, it took 5 hours or more until the hydrolysis completed when the additives were not added or an alkali agent was used.

Upon further stirring, the methylsilanetriol polymerizes to increase the molecular weight and becomes insoluble in a water-ethanol solution, whereby the solution becomes clouded. If the period of time required for the clear solution to become clouded is short, the methylsilanetriol does not sufficiently penetrate into hair but polymerizes in the vicinity of the surface of hair to fail to give strength/body-providing effect on hair. The time required for the clear solution to become clouded was measured and shown in Table 1.

TABLE 1

| | Additives | pKa1 | Time required for clear solution after hydrolysis to become clouded |
|---|---|---|---|
| Organic acid | Aspartic acid | 1.93 | not less than 1 hour but less than 3 hours |
| | Salicylic acid | 2.81 | not less than 1 hour but less than 3 hours |
| | Tartaric acid | 2.82 | not less than 1 hour but less than 3 hours |
| | Fumaric acid | 2.85 | not less than 1 hour but less than 3 hours |
| | Citric acid | 2.90 | not less than 1 hour but less than 3 hours |
| | Malic acid | 3.24 | not less than 1 hour but less than 3 hours |
| | Formic acid | 3.55 | not less than 3 hours but less than 5 hours |
| | Lactic acid | 3.66 | not less than 3 hours but less than 5 hours |
| | Succinic acid | 4.00 | not less than 3 hours but less than 5 hours |
| | Glutaric acid | 4.13 | not less than 5 hours |
| | Adipic acid | 4.26 | not less than 5 hours |
| | Acetic acid | 4.56 | not less than 5 hours |
| | Propionic acid | 4.67 | not less than 5 hours |
| Inorganic acid | Hydrochloric acid | | less than 1 hour |
| | Phosphoric acid | | less than 1 hour |
| Alkali | Sodium hydroxide | | less than 1 hour |
| | Ammonia | | less than 1 hour |

As apparent from Table 1, a silanol compound rapidly polymerizes after the hydrolysis to fail to penetrate into hair when an inorganic acid or an alkali agent is used as an additive.

Example 1

Processing of Hair not having a Record of Chemical Treatment

In a 300 mL eggplant-shaped flask, 75.0 g of ion-exchange water was weighed and placed, and 0.01 g of adipic acid was added thereto and dissolved therein by stirring at room temperature to give a second agent (pH 4.0). The second agent was mixed with a first agent including 25.0 g of methyltriethoxysilane. The resulting mixture was stirred in a thermostatic tank kept at 40° C. using a stirring bar equipped with stirring blades having a half-moon shape of 7 cm and made of Teflon (registered trademark) at a stirring speed of 200 rpm for 3 hours. Upon allowing to stand, the mixture initially separated into two phases but turned into a uniform aqueous solution after completion of a reaction to give an aimed aqueous solution containing a silanol. It was confirmed that the resulting aqueous solution contained 14% by weight of methylsilanetriol by $^{29}$Si—NMR. The resulting aqueous solution had a pH of 4.0.

Using the hair not having a record of any chemical treatment obtained from a westerner, a bundle of hair (5 g) was prepared. Then, 10 g of the above-mentioned aqueous solution containing the silanol was evenly applied to the bundle. The bundle was allowed to stand at room temperature for 1 hour, and dried and hardened for 15 minutes by means of a hot-air dryer. Thereafter, the bundle was washed with a shampoo having the composition shown in Table 2, treated with a hair conditioner having the composition shown in Table 3 and then dried.

TABLE 2

| Shampoo | Formulation (% by weight) |
|---|---|
| 25 wt. % Aqueous solution of sodium polyoxyethylene (2.5) lauryl ether sulfate | 62.00 |
| Lauric acid diethanolamide | 2.28 |
| Disodium edetate | 0.10 |
| Sodium benzoate | 0.50 |
| Oxybenzone | 0.03 |
| Phosphoric acid (75 wt % aqueous solution) | 0.10 |
| Dibutylhydroxytoluene | 0.01 |
| Sodium chloride | 0.80 |
| Red No. 106 | 0.00012 |
| Perfume | 0.26 |
| Purified water | Balance |

TABLE 3

| Hair conditioner | Formulation (% by weight) |
|---|---|
| Stearyltrimethylammonium chloride (28 wt % aqueous solution) | 3.0 |
| Cetanol | 3.0 |
| Propylene glycol | 3.0 |
| Methyl paraffin | 0.1 |
| Purified water | Balance |

Figure 2:
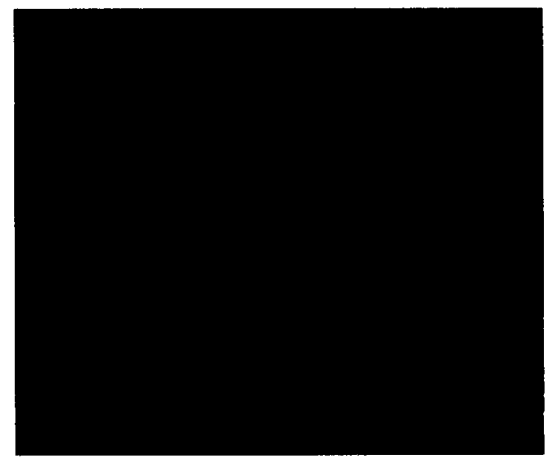
FIG. 2 is an FE-SEM-EDS elemental silicon mapping of the cross-section of an unprocessed hair.

An FE-SEM-EDS elemental silicon mapping of the cross-section of the hair after the above processing is shown in FIG. 1. Also, an FE-SEM-EDS elemental silicon mapping of the cross-section of the unprocessed hair is shown in FIG. 2. The FE-SEM-EDS elemental silicon mapping herein means a mapping of elemental silicon on the cross-section of hair conducted by means of an apparatus in which an EDS (energy-dispersing type X-ray spectrometer) is attached to a FE-SEM (field emission scanning electron microscope).

From the elemental silicon mapping, penetration of silicon compounds into the hair after processing with a cosmetic composition was evaluated. It was confirmed that the compounds penetrated into the center of the hair.

Further, the amount of silicon compound absorbed to the hair (amount of elemental silicon absorbed) was measured to find that it was 2.5 to 3.0% by weight of the weight of the hair.

Furthermore, the hair after processing with a cosmetic composition was subjected to a bending elasticity test according to the following method. As a result, an increase of bending elasticity by 40 to 50% relative to unprocessed hair was shown. In addition, it was felt that a bundle of hair after processing with a cosmetic composition was increased in strength/body according to feeling by hands. This feeling was retained after shampooing was repeated 3 to 5 times.

<Method of Evaluating Amount of Silicon Compounds Absorbed to Hair>

For evaluation of the amount of silicon compounds absorbed to hair, "ICP (inductive coupling plasma) optical emission analyzer (JY238ULTRACE, HORIBA)" was used. The amount of absorbed silicon compounds was obtained as an amount of absorbed elemental silicon based on the amount of elemental silicon measured by an ash making/alkali fusing/ICP method.

A sample in an amount of 0.1 g is taken in a platinum crucible and, after carbonization by a heater until no smoke is generated, it is incinerated in an electric furnace at 550° C. for 2 hours. After cooling, 1 g of an alkali fusing agent ($Na_2CO_3$: $H_3BO_3$=5:2) was added to the remaining ash and alkali melting was effected in an electric furnace at 950° C. for 30 minutes. After cooling, the product was dissolved in 4 ml of 6N hydrochloric acid and was added with water to give 50 ml of a sample solution. The sample was measured 3 times at an absorption wavelength of 251.612 nm for an integral time of 3 seconds, and from the average value, the amount of elemental silicon was obtained by using an analytical curve. Calculation of the amount of elemental silicon absorbed to hair is based on the following equation.

Amount of absorbed elemental silicon (%)=[amount of elemental silicon (mg)/weight of hair (g)]×0.1

<Method of Bending Elasticity Test>

"Pure bending tester (KES-FB2-S, Kato Tech Co., Ltd.)" was used for the bending elasticity test, and the force required for bending hair (bending elasticity) was measured.

Figure 3:
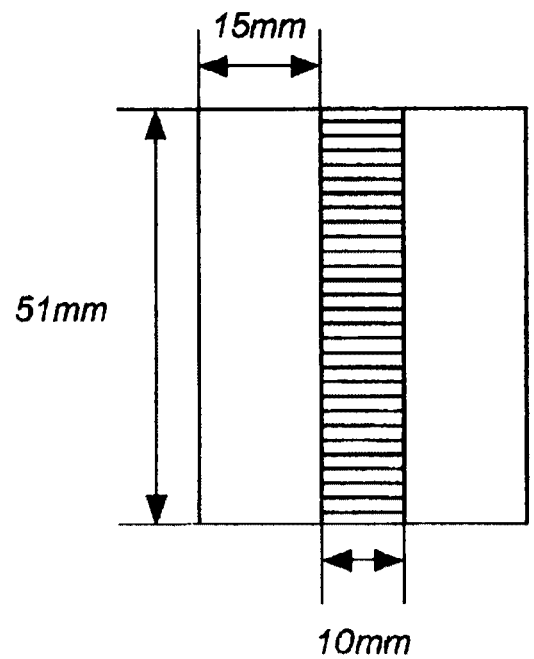
FIG. 3 shows a sample for measurement used in a bending elasticity test.

Both ends of hair were cut off and only the hair of 5 cm or more in length was used for the evaluation test. Prior to measurement, the hair was placed in an atmosphere having a relative humidity of 65% for at least 24 hours. As shown in FIG. 3, two sheets of graph paper of 51 mm in length and 15 mm in width which were laid side-by-side at a distance of 10 mm and to which 50 pieces of human hair were adhered were used as a sample for measurement. The sample was attached to the pure bending tester and a bending elasticity was measured. The measuring conditions were as follows: 20° C., relative humidity: 65%, sensitivity: 2×1, maximum bending curvature: 2.5 cm$^{-1}$. Bending elasticity was obtained from the slope of the straight line obtained by collinearly approximating the force required for bending one filament of hair having a curvature between 1.0 and 2.0 cm$^{-1}$.

Example 2

Processing of Hair having a Record of Chemical Treatment

To a bundle of hair (20 cm, 10 g) not having a record of chemical treatment obtained from a westerner was applied Lavenus High Bleach (Kao Corporation), and the bundle was heat-treated at 60° C. for 30 minutes, then washed with Emal 20 CM-S (Kao Corporation, a product containing 25% by weight of sodium polyoxyethylene alkyl ether sulfate), and dried naturally. The bleaching treatment was repeated a predetermined number of times on the bundle to obtain hair having a record of chemical treatment.

Thereafter, the hair was processed using a hair processing composition similar to that in Example 1 by a method similar to that in Example 1. The amount of absorbed elemental silicon after processing was measured similarly to Example 1. The results are shown in Table 4.

Figure 4:
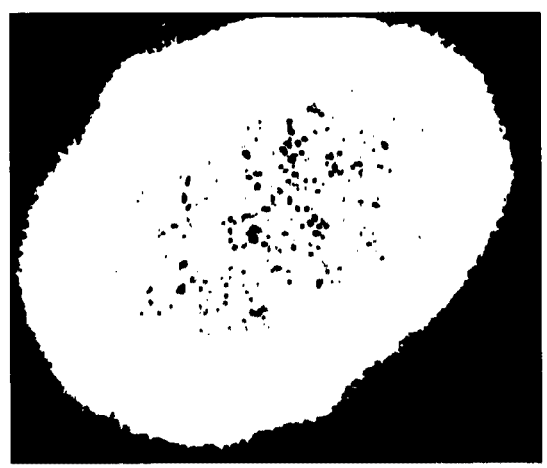
FIG. 4 is an FE-SEM-EDS elemental silicon mapping of the cross-section of the hair after subjecting to the process of Example 2.

In addition, an FE-SEM-EDS elemental silicon mapping of the cross-section of the hair which was subjected to bleach-treatment 3 times and then processed with the hair processing composition of the invention is shown in FIG. 4. From the elemental silicon mapping, it was confirmed that the silicon compounds had penetrated into the center of the hair.

TABLE 4

| | Number of bleaching | | | |
|---|---|---|---|---|
| | 0 time | One time | Two times | Three times |
| Amount of absorbed elemental silicon (%) | 2.5 | 2.8 | 3.5 | 4.3 |

As apparent from Table 4, the amount of absorbed elemental silicon after processing with the cosmetic composition of the invention increased as the number of bleaching increased.

Comparative Example 1

75.0 g of 0.1 mol/L hydrochloric acid used as the second agent and 25.0 g of methyltriethoxysilane used as the first agent were placed in a 300 ml eggplant-shaped flask, and were stirred using a stirring bar equipped with stirring blades having a half-moon shape of 7 cm and made of Teflon (registered trademark) at a stirring speed of 200 rpm. Upon allowing to stand, the mixture initially separated into two phases but turned into a uniform aqueous solution by continuously stirring to give an aimed hair processing composition including an aqueous solution of silanol (pH 1).

Figure 5:
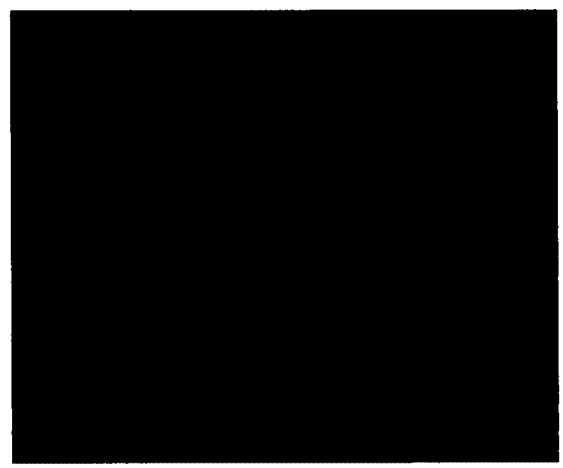
FIG. 5 is an FE-SEM-EDS elemental silicon mapping of the cross-section of the hair after subjecting to the process of Comparative Example 1.

Using the hair processing composition thus obtained, hair was treated similarly to the method of Example 1 to give processed hair. An FE-SEM-EDS elemental silicon mapping of the cross-section of the hair thus obtained is shown in FIG. 5. From the mapping, it was seen that the silicon compounds were present on the surface of the hair and did not penetrate into the inside of the hair. The amount of absorbed elemental silicon was measured similarly to the method of Example 1 and was found to be 3500 ppm, which was less than the amount in Example 1 in which silicon compounds penetrated into the inside of the hair.

Comparative Example 2

To 75.0 g of ion-exchange water (pH 6.6) was added 25.0 g of methyltriethoxysilane, and the resulting mixture was stirred using a stirring bar equipped with stirring blades having a half-moon shape of 7 cm and made of Teflon (registered trademark) at a stirring speed of 200 rpm at room temperature. Stirring was continued to obtain a uniform aqueous solution from a reaction mixture having separated two phases. However, it was not possible to obtain an aimed uniform clear aqueous solution but a white turbid aqueous solution in which silicon compounds were considered to be partially polymerized was obtained.

Hair was processed with this white turbid aqueous solution similarly to the method of Example 1 to obtain processed hair. The amount of absorbed elemental silicon was measured similarly to the method of Example 1 to find that it was not more than 50 ppm. No difference in the absorbed amount was found between the processed hair and unprocessed hair.

Figure 6:
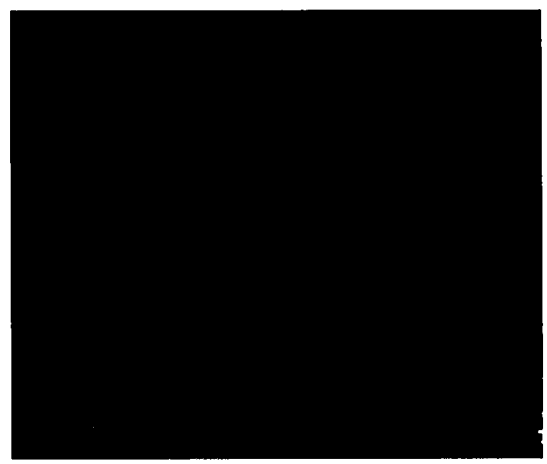
FIG. 6 is an FE-SEM-EDS elemental silicon mapping of the cross-section of the hair after subjecting to the process of Comparative Example 3.

To 25.0 g of methyltriethoxysilane was added 75.0 g of ethanol to give a hair processing solution. Using the solution, hair was processed similarly to the method of Example 1 to give a processed hair. An FE-SEM-EDS elemental silicon mapping of the cross-section of the hair thus obtained is shown in FIG. 6. From the mapping, it was not possible to confirm the presence of silicon compounds on the surface or inside of the hair. The amount of absorbed elemental silicon was measured similarly to the method of Example 1 to find that it was not more than 50 ppm. No difference in the absorbed amount was found between the processed hair and unprocessed hair.

Test Example 2

Miscibility and Speed of Hydrolysis when a Surfactant is Concomitantly Used

A hair processing composition (pH: 3.5-3.8; 20° C.) including 25.0% by weight of methyltriethoxysilane, 0.8% by weight of adipic acid, 10% by weight of a surfactant shown in Table 5 and a balance of ion-exchange water was prepared. Immediately thereafter, 30 ml of the hair processing composition was placed in a 50 ml sealed vessel, stirred (by shaking the vessel 30 times), and then allowed to stand. Observation was effected every 5 minutes and stirring was effected again when separation occurred. Incidentally, the pH (25° C.) was measured by a pH meter manufactured by HORIBA.

As controls, two samples of a hair processing composition including 25.0% by weight of methyltriethoxysilane, 0.8% by weight of adipic acid and a balance of ion-exchange water and not containing any surfactant were prepared. One of the samples was subjected to a stirring operation similar to the above and the other was continuously stirred by a magnetic stirrer.

[Evaluation of Miscibility]

The state of a mixed liquid 5 minutes after the initial stirring by shaking was shown in Table 5. The "emulsified" in the table shows the state wherein the whole solution is uniformly white turbid (clouded) visually. The "partially emulsified" shows the state wherein apart of the upper layer or lower layer of the solution is white turbid and the remainder is clear. The "two phase separation" shows the state wherein a clear liquid is separated into upper and lower phases accompanied by a border line.

[Evaluation of Speed of Hydrolysis]

The time required for the mixed liquid to turn into a uniform clear solution after initial stirring by shaking was shown in the table.

Incidentally, each hair processing composition was applied, to hair after mixing while stirring the first agent and the second agent to give a mixture having a clear appearance.

(1) Evaluation of the Amount of Silicon Compounds Absorbed to Hair, and Bending Elasticity Test Using a hair not having a record of any chemical treatment obtained from a westerner, a bundle of hair (5 g) was prepared. Then, 10 g of a hair processing composition shown in Table 6 was evenly applied to the bundle. The bundle was wrapped with a wrapping and allowed to stand in an oven at 48° C. for 1 hour. Thereafter, an excess amount of the hair processing composition was removed by a towel and dried completely for 15 minutes by means of a hot-air dryer to polymerize the silanol compounds in the hair. Thereafter, the bundle was treated with the same shampoo and rinse as those used in Example 1 and then dried.

Similarly to Example 1, evaluation of the amount of silicon compounds absorbed to hair and a bending elasticity test were conducted.

(2) Organoleptic Evaluation

Evaluation on "enhanced feeling of strength/body of hair" and "manageability of hair" was conducted by ten expert panelists in accordance with the following ranking criterion, and the total values were shown.

TABLE 5

| Hair processing composition | | Surfactant | HLB | Miscibility | Stirring frequency | Hydrolysis time (minutes) |
|---|---|---|---|---|---|---|
| 1 | Nonionic | Polyoxyethylene (4) lauryl ether | 9.6 | Partially emulsified | Once every 5 minutes by hand shaking | 20 |
| 2 | | Polyoxyethylene (6) lauryl ether | 10.5 | Emulsified | Only initial stirring | 15 |
| 3 | | Polyoxyethylene (8) lauryl ether | 12.1 | Emulsified | Only initial stirring | 10 |
| 4 | | Polyoxyethylene (9) lauryl ether | 13.6 | Emulsified | Only initial stirring | 15 |
| 5 | | Polyoxyethylene (20) lauryl ether | 15.3 | Partially emulsified | Once every 5 minutes by hand shaking | 20 |
| 6 | | Polyoxyethylene (23) lauryl ether | 16.9 | Partially emulsified | Once every 5 minutes by hand shaking | 20 |
| 7 | Cationic | Lauryltrimethyl-ammonium chloride | | Emulsified | Only initial stirring | 10 |
| 8 | Amphoteric | Lauryldimethylamino-acetic acid betaine | | Partially emulsified | Once every 5 minutes by hand shaking | 15 |
| 9 | Anionic | Sodium lauryl sulfate | | Emulsified | Only initial stirring | 10 |
| 10 | | Sodium polyoxyethylene (1) lauryl sulfate | | Emulsified | Only initial stirring | 10 |
| 11 | | Ammonium polyoxyethylene (2) lauryl sulfate | | Partially emulsified | Once every 5 minutes by hand shaking | 15 |
| 12 | | None | | Two phase separation | Once every 5 minutes by hand shaking | Not less than 360 |
| 13 | | None | | Two phase separation | Continuous stirring (stirrer) | 30 |

Example 3

Processing of Hair with a Hair Processing Composition Containing a Surfactant

A first agent including an alkoxysilane and a second agent including an acid, water, a surfactant and a pH regulator (sodium hydroxide) were mixed to give the hair processing compositions shown in Table 6. The hair processing compositions were subjected to the evaluation shown below. The results are also shown in Table 6.

<Enhanced Feeling of Strength/Body of Hair>
(Compared with an Unprocessed Hair, a Processed Hair is)
   3: felt to be apparently more supple and tough.
   2: felt to be supple and tough.
   1: felt to be slightly more supple and tough.
   0: not felt to be more supple and tough.
   −1: felt to be less supple and tough.

<Manageability of Hair>
(Compared with an Unprocessed Hair, a Processed Hair is)
   3: felt to be apparently more manageable.
   2: felt to be manageable.
   1: felt to be slightly more manageable.
   0: not felt to be more manageable.
   −1: felt to be less manageable.

TABLE 6

| | Hair processing composition (content is based on "wt. %") | | | | | | | | | |
|---|---|---|---|---|---|---|---|---|---|---|
| | 14 | 15 | 16 | 17 | 18 | 19 | 20 | 21 * | 22 * | 23 * |
| Dimethyldiethoxysilane | — | — | — | — | — | 10 | 20 | — | — | — |
| Methyltriethoxysilane | 25 | 25 | 25 | 25 | 40 | 20 | 20 | 25 | 25 | 25 |
| Adipic acid | 1 | 1 | 1 | 0.5 | 1 | 1 | 1 | — | 1 | — |
| Acetic acid | — | — | — | 0.5 | — | — | — | — | — | — |
| Hydrochloric acid (0.1 mol/L) | — | — | — | — | — | — | — | — | — | 60 |
| Polyoxyethylene (9) lauryl ether | 10 | — | 10 | 5 | 10 | 10 | 10 | — | — | — |
| Sodium lauryl sulfate | — | 10 | — | 5 | — | — | — | — | — | — |
| 30 wt. % Sodium hydroxide | q.s. | q.s. | q.s. | q.s. | q.s. | q.s. | q.s. | q.s. | q.s. | — |
| Ion-exchange water | Bal | Bal | Bal | Bal | Bal | Bal | Bal. | Bal. | Bal. | Bal. |
| pH | 3.1 | 3.1 | 3.1 | 3.1 | 3.1 | 3.1 | 3.1 | 3.1 | 3.1 | 1 |
| Bending elasticity enhancement ratio (processed/unprocessed) | 1.2 | 1.2 | 1.3 | 1.3 | 1.4 | 1.2 | 1.1 | 1 | 1.1 | 1 |
| Amount of silicon absorbed to hair (wt. %) | 2.2 | 2.2 | 2.2 | 2.4 | 3.3 | 2.8 | 2.6 | Less than 0.1 | 1.8 | Less than 0.3 |
| Enhanced feeling of strength/body of hair | 20 | 19 | 21 | 21 | 25 | 24 | 22 | 3 | 18 | 2 |
| Manageability of hair | 16 | 15 | 20 | 18 | 22 | 20 | 26 | 1 | 16 | 3 |

* Comparative product

Test Example 3

Polymerization Time when a Polymerization Accelerator is Concomitantly Used If a silanol compound is dehydrated and condensed to increase its molecular weight, the resulting solution becomes insoluble and thus becomes clouded. Accordingly, by checking the time until the solution becomes clouded, the time required for polymerization can be estimated. Thus, 50 g of a hair processing composition shown in Table 7 and 50 g of a polymerization accelerator shown in Table 8 were placed in a glass vessel and the time until the solution becomes clouded while stirring at room temperature (25° C.) was checked. Incidentally, the polymerization accelerator was added after the hair processing composition had become to have a one uniform phase by mixing while stirring.

TABLE 7

| Hair processing composition (wt. %) | 24 | 25 |
|---|---|---|
| Methyltriethoxysilane | 25.0 | 40 |
| Adipic acid | 0.75 | 0.75 |
| Purified water | 74.25 | 59.25 |
| pH | 3.3 | 3.4 |

TABLE 8

| | Polymerization accelerator (content is based on "wt. %") | | | | | | | | | | |
|---|---|---|---|---|---|---|---|---|---|---|---|
| | 1 | 2 | 3 | 4 | 5 | 6 | 7 | 8 | 9 | 10 | 11 |
| Citric acid | 5.0 | — | — | — | — | — | 5.0 | — | — | — | — |
| Malic acid | — | 5.0 | — | — | — | — | — | 5.0 | — | 10.0 | — |
| Lactic acid | — | — | 5.0 | — | — | — | — | — | 4.5 | — | — |
| Phosphoric acid | — | — | — | 1.0 | — | — | — | — | — | — | 5.0 |
| 2-Amino-2-methyl-1-propanol | — | — | — | — | 1.0 | — | — | — | — | — | — |
| Monoethanolamine | — | — | — | — | — | 1.0 | — | — | — | — | — |
| Sodium hydroxide | — | — | — | — | — | — | q.s. | q.s. | q.s. | q.s. | q.s. |
| Purified water | Bal. | Bal. | Bal. | Bal. | Bal. | Bal. | Bal. | Bal. | Bal. | Bal. | Bal. |
| pH | 1.7 | 1.8 | 1.9 | 1.6 | 11.6 | 11.5 | 3.0 | 3.0 | 3.0 | 3.0 | 3.0 |
| Mixed hair processing composition | 24 | 24 | 24 | 24 | 24 | 24 | 24 | 24 | 24 | 24 | 24 |
| pH when mixed with a hair processing composition at a ratio of 1:1 | 2.0 | 2.1 | 2.1 | 1.9 | 8.5 | 9.2 | 3.3 | 3.2 | 3.2 | 3.3 | 3.2 |
| Time until polymers produced (minutes) (time until a mixed solution becomes clouded) | 30 | 34 | 48 | 70 | 10 | 1 | 120 | 120 | 70 | 30 | 240 |

| | Polymerization accelerator (content is based on "wt. %") | | | | | | | | |
|---|---|---|---|---|---|---|---|---|---|
| Polymerization accelerator (wt. %) | 12 | 13 | 14 | 15 | 16 | 17 | 18* | 19* | 20* |
| Malic acid | 5.0 | 10.0 | — | — | 5.0 | 10.0 | — | — | — |
| Hydrochloric acid | — | — | 0.36 | — | — | — | — | — | — |
| Sodium hydrogen carbonate | — | — | — | 5.0 | — | — | — | — | — |
| 2-Amino-2-methyl-1-propanol | — | — | — | — | — | — | — | 0.5 | — |
| Sodium hydroxide | q.s. | q.s. | — | q.s. | q.s. | q.s. | — | — | 0.5 |
| Purified water | Bal. | Bal. | Bal. | Bal. | Bal. | Bal. | 100 | Bal. | Bal. |
| pH | 2.0 | 2.0 | 1.1 | 10.0 | 2.0 | 2.0 | 6.9 | 11.3 | 13.8 |

TABLE 8-continued

| Mixed hair processing composition | 24 | 24 | 24 | 24 | 25 | 25 | 24 | 24 | 24 |
|---|---|---|---|---|---|---|---|---|---|
| pH when mixed with a hair processing composition at a ratio of 1:1 | 2.2 | 2.2 | 1.3 | 9.8 | 2.3 | 2.4 | 3.3 | 5.1 | 12.4 |
| Time until polymers produced (minutes) (time until a mixed solution becomes clouded) | 32 | 23 | 22 | 1 | 45 | 25 | 1 day or more | 1 day or more | 1 day or more |

*Comparative product

Examples 4-7 and Comparative Example 4

In the following examples and comparative example, the hair processing compositions and the polymerization accelerators shown in Table 9 were used to process hair and the amount of silicon compounds absorbed to the hair was evaluated.

TABLE 9

| Hair processing composition (wt. %) | a | b | c |
|---|---|---|---|
| Methyltriethoxysilane | 25 | 40 | 40 |
| Adipic acid | 0.75 | 0.75 | 0.75 |
| Hydroxypropyl xanthan gum | — | — | 0.5 |
| Polyoxyethylene (9) lauryl ether | — | — | 3.0 |
| Purified water | Bal. | Bal. | Bal. |
| pH | 3.3 | 3.4 | 4.2 |

| Polymerization accelerator (wt. %) | a | b |
|---|---|---|
| Malic acid | 5.0 | 10.0 |
| Sodium hydroxide | — | q.s. |
| Purified water | Bal. | Bal. |
| pH | 1.8 | 3.0 |

Example 4

To 3 g of a bundle of hair not having a record of chemical treatment was applied 3 g of hair processing composition "a". Thereafter, the bundle was wrapped with a wrapping so that the composition did not dry and was allowed to stand at room temperature (25° C.) for 30 minutes. Hair processing composition "a" was removed by a towel, and after uniformly applying 3 g of polymerization accelerator "a", the bundle was wrapped with a wrapping so that the accelerator did not dry, and the bundle was allowed to stand for 30 minutes. Thereafter, the bundle was washed with a shampoo not containing a silicone and sufficiently dried, and then the amount of silicon adhered to and penetrated into the hair was determined. An ICP (induction plasma) optical emission analyzer was used for the measurement of the amount of silicon absorbed to the hair. The amount of silicon absorbed to the processed hair was 0.4% by weight. Incidentally, the pH of a mixture of hair processing composition "a" and polymerization accelerator "a" at a weight ratio of 1:1 is 2.1.

Example 5

To 3 g of a bundle of hair not having a record of chemical treatment was applied 3 g of hair processing composition "a". Thereafter, the bundle was wrapped with a wrapping so that the composition did not dry and was allowed to stand at room temperature (25° C.) for 30 minutes. Hair processing composition "a" was removed by a towel, and after uniformly applying 3 g of polymerization accelerator "a", the bundle was wrapped with a wrapping so that the accelerator did not dry, and was allowed to stand for 30 minutes. Thereafter, the bundle was washed with a shampoo not containing a silicone and sufficiently dried. After repeating the processing starting from the application of the hair processing agent to shampooing three times, the amount of silicon adhered to and penetrated into the hair was determined. An ICP (induction plasma) optical emission analyzer was used for the measurement of the amount of silicon absorbed to the hair. The amount of silicon absorbed to the processed hair was 1.6% by weight. By repeating the processing, the amount of absorbed silicon increased. Incidentally, the pH of a mixture of hair processing composition "a" and polymerization accelerator "a" at a weight ratio of 1:1 is 2.1.

Example 6

To 3 g of a bundle of hair not having a record of chemical treatment was applied 3 g of hair processing composition "b". Thereafter, the bundle was wrapped with a wrapping so that the composition did not dry and was allowed to stand at room temperature (25° C.) for 30 minutes. Hair processing composition "b" was removed by a towel and, after uniformly applying 3 g of polymerization accelerator "b", the bundle was wrapped with a wrapping so that the accelerator did not dry, and was allowed to stand for 30 minutes. Thereafter, the bundle was washed with a shampoo not containing a silicone and sufficiently dried, and then the amount of silicon adhered to and penetrated into the hair was determined. An ICP (induction plasma) optical emission analyzer was used for the measurement of the amount of silicon absorbed to the hair. The amount of silicon absorbed to the treated hair was 1.20% by weight. By increasing the amount of a silicon compound contained in a hair processing composition, the amount of absorbed silicon increased. Incidentally, the pH of a mixture of hair processing composition "b" and polymerization accelerator "b" at a weight ratio of 1:1 is 3.1.

Example 7

Hair of a woman with long hair having a record of hair coloring and hair straightening perm was divided into two parts from the middle of the hair by a comb. After one part of the hair was uniformly applied with hair processing composition "c", the treated part was wrapped with a wrapping and was allowed to stand for 30 minutes with heating to 48° C. by a head heater (roller ball). Hair processing composition "c" was removed by a towel. After uniformly applying polymerization accelerator "b", the treated part was allowed to stand at room temperature (25° C.) for 15 minutes. Thereafter, the treated part was washed with a shampoo not containing a silicone and sufficiently dried. The appearance and feeling each of the processed hair and unprocessed hair were evaluated. The amount of silicon adhered to and penetrated into the hair was determined. An ICP (induction plasma) optical emission analyzer was used for the measurement of the amount of silicon absorbed to the hair. Compared with the unprocessed hair, the processed hair was apparently enhanced in flexibility, controlled in generation of flyaways hair and strays hair, and was manageable in appearance. The amount of silicon absorbed to the processed hair was 2.09% by weight. By heating the hair after application of the hair processing composition, the amount of absorbed silicon increased. Incidentally, the pH of a mixture of hair processing composition "c" and polymerization accelerator "b" at a weight ratio of 1:1 is 3.1.

Comparative Example 4

To 3 g of a bundle of hair not having a record of chemical treatment was applied 3 g of hair processing composition "a". Thereafter, the bundle was wrapped with a wrapping so that the composition did not dry and was allowed to stand at room temperature (25° C.) for 30 minutes. The bundle was washed with a shampoo not containing a silicone and sufficiently dried, and then the amount of silicon adhered to and penetrated into the hair was determined. An ICP (induction plasma) optical emission analyzer was used for the measurement of the amount of silicon absorbed to the hair. The amount of silicon absorbed to the processed hair was 0.19% by weight.

The invention claimed is:

1. A method for processing hair, which comprises:
   mixing while stirring a hair processing composition comprising an alkoxysilane of formula (1)

$$R^1_p Si(OR^2)_{4-p} \quad (1)$$

wherein $R^1$ and $R^2$ represent a straight or branched alkyl group having 1 to 6 carbon atoms or a straight or branched alkenyl group having 2 to 6 carbon atoms, p "$R^1$"(s) and (4–p) "$R^2$"(s) may be the same or different, and p represents an integer of from 0 to 2; an organic acid and water wherein said hair processing composition has a pH of 2 to 4.2, until said composition has one uniform phase,
   applying said composition to hair within 30 minutes after mixing to allow a water soluble silanol compound of formula (2):

$$R^1_p Si(OH)_n (OR^2)_{4-p-n} \quad (2)$$

wherein $R^1$, $R^2$ and p have the same meaning as above, n is an integer of not less than 1 and not more than (4–p), and p "$R^1$"(s) and (4–p–n) "$R^2$"(s) may be the same or different and having a molecular weight of 300 or less and generated through the acidic hydrolysis of the alkoxysilane of formula (1), to penetrate into said hair and polymerize,
   wherein said composition is retained on said hair for 15 to 90 minutes,
   wherein said organic acid is at least one selected from the group consisting of oxalic acid, maleic acid, aspartic acid, salicylic acid, tartaric acid, fumaric acid, citric acid, malic acid, succinic acid, formic acid, lactic acid, glutaric acid, adipic acid, and propionic acid, and
   wherein the organic acid content in said mixing ranges from 0.001 to 5 wt %.

2. A method for processing hair, which comprises:
   mixing while stirring a hair processing composition comprising a first agent comprising an alkoxysilane of formula (1):

$$R^1_p Si(OR^2)_{4-p} \quad (1)$$

wherein $R^1$ and $R^2$ represent a straight or branched alkyl group having 1 to 6 carbon atoms or a straight or branched alkenyl group having 2 to 6 carbon atoms, p "$R^1$"(s) and (4–p) "$R^2$"(s) may be the same or different, and p represents an integer of from 0 to 2; and a second agent comprising an organic acid and water wherein said hair processing composition has a pH of 2 to 4.2, until said composition has one uniform phase,
   applying said composition to hair within 30 minutes after mixing to allow a water soluble silanol compound of formula (2):

$$R^1_p Si(OH)_n (OR^2)_{4-p-n} \quad (2)$$

wherein $R^1$, $R^2$ and p have the same meaning as above, n is an integer of not less than 1 and not more than (4–p), and p "$R^1$"(s) and (4–p–n) "$R^2$"(s) may be the same or different and having a molecular weight of 300 or less and generated through the acidic hydrolysis of the alkoxysilane of formula (1), to penetrate into said hair and polymerize
   wherein said composition is retained on said hair for 15 to 90 minutes,
   wherein said organic acid is at least one selected from the group consisting of oxalic acid, maleic acid, aspartic acid, salicylic acid, tartaric acid, fumaric acid, citric acid, malic acid, succinic acid, formic acid, lactic acid, glutaric acid, adipic acid, and propionic acid, and
   wherein the organic acid content in said mixing ranges from 0.001 to 5 wt %.

3. The method of claim 1, wherein said hair processing composition further comprises a surfactant.

4. The method of claim 1, further comprising heating said hair to which said composition is applied.

5. A method for processing hair, which comprises:
   mixing while stirring a hair processing composition ($A_1$) comprising an alkoxysilane of formula (1):

$$R^1_p Si(OR^2)_{4-p} \quad (1)$$

wherein $R^1$ and $R^2$ represent a straight or branched alkyl group having 1 to 6 carbon atoms or a straight or branched alkenyl group having 2 to 6 carbon atoms, p "$R^1$"(s) and (4–p) "$R^2$"(s) may be the same or different, and p represents an integer of from 0 to 2; an organic acid and water wherein said hair processing composition ($A_1$) has a pH of 2 to 4.2, until said composition has one uniform phase,
   applying to hair within 30 minutes of said mixing, a hair processing composition ($A_2$) which is produced after said alkoxysilane is hydrolyzed and converted to a water-soluble silanol compound of formula (2):

$$R^1_p Si(OH)_n (OR^2)_{4-p-n} \quad (2)$$

wherein $R^1$, $R^2$ and p have the same meaning as above, n is an integer of not less than 1 and not more than (4–p), and p "$R^1$"(s) and (4–p–n) "$R^2$"(s) may be the same or different and having a molecular weight of 300 or less
   applying as a polymerization accelerator an acidic aqueous solution ($B_a$) which, when mixed with the hair processing composition ($A_2$) at a weight ratio of 1:1, makes the pH of the hair processing composition ($A_2$) in a range of from 1 to 4
   wherein said hair processing composition ($A_2$) is retained on said hair for 10 to 90 minutes and
   wherein said water-soluble silanol compound is allowed to penetrate into said hair and polymerize,
   wherein said organic acid is at least one selected from the group consisting of oxalic acid, maleic acid, aspartic acid, salicylic acid, tartaric acid, fumaric acid, citric acid, malic acid, succinic acid, formic acid, lactic acid, glutaric acid, adipic acid, and propionic acid, and
   wherein the organic acid content in said mixing ranges from 0.001 to 5 wt %.

6. The method of claim 5 wherein said acidic aqueous solution (Ba) comprises an acid having a first dissociate index (pKa1) which is less than 4.1.

7. The method of claim 5, wherein after mixing said hair processing composition ($A_1$), organic acid and water have a pH of 2 to 4.

8. A method for processing hair, which comprises:
mixing while stirring a hair processing composition ($A_1$) comprising an alkoxysilane of formula (1):

  (1)

wherein $R^1$ and $R^2$ represent a straight or branched alkyl group having 1 to 6 carbon atoms or a straight or branched alkenyl group having 2 to 6 carbon atoms, p "$R^1$"(s) and (4−p) "$R^2$"(s) may be the same or different, and p represents an integer of from 0 to 2; an organic acid and water, until said composition has one uniform phase, wherein after mixing; said hair processing composition ($A_1$), organic acid and water have a pH of 2 to 4.2, applying to hair within 30 minutes of said mixing, a hair processing composition ($A_2$) which is produced after said alkoxysilane is hydrolyzed and converted to a water-soluble silanol compound of formula (2):

  (2)

wherein $R^1$, $R^2$ and p have the same meaning as above, n is an integer of not less than 1 and not more than (4−p), and p "$R^1$"(s) and (4−p−n) "$R^2$"(s) may be the same or different and having a molecular weight of 300 or less applying as a polymerization accelerator an alkaline aqueous solution ($B_b$) which, when mixed with the hair processing composition ($A_2$) at a weight ratio of 1:1, makes the pH of the hair processing composition ($A_2$) in a range of from 8 to 12 wherein said hair processing composition ($A_2$) is retained on said hair for 10 to 90 minutes and wherein said water-soluble silanol compound is allowed to penetrate into said hair and polymerize, wherein said organic acid is at least one selected from the group consisting of oxalic acid, maleic acid, aspartic acid, salicylic acid, tartaric acid, fumaric acid, citric acid, malic acid, succinic acid, formic acid, lactic acid, glutaric acid, adipic acid, and propionic acid, and wherein the organic acid content in said mixing ranges from 0.001 to 5 wt %.

9. The method of claim 8, wherein said organic acid has a first dissociation index (pKa1) in a range of from 4.1 to 5.

10. The method of claim 8, wherein said hair processing composition ($A_1$) comprises a first agent comprising said alkoxysilane and a second agent comprising said organic acid and water.

11. The process according to claim 8, further comprising heating said hair to which said composition ($A_2$) is applied.

12. The process according to claim 8, further comprising heating said hair to which said composition ($A_2$) is applied after said polymerization accelerator is applied.

13. The process of claim 8, wherein after mixing said hair processing composition ($A_1$), organic acid and water have a pH of 2 to 4.

14. The method of claim 1, wherein said hair processing composition has a pH of 3 to 4.

15. The method of claim 2, wherein said hair processing composition further comprises a surfactant.

16. The method of claim 2, further comprising heating said hair to which said composition is applied.

17. The method of claim 2, wherein said hair processing composition has a pH of 3 to 4.

18. The method of claim 3, further comprising heating said hair to which said composition is applied.

19. The method of claim 5, wherein said hair processing composition ($A_2$) has a pH of 1.5 to 3.5.

20. The method of claim 5, wherein said hair processing composition ($A_2$) has a pH of 2 to 3.3.

21. The method of claim 5, wherein said hair processing composition ($A_1$) has a pH of 3 to 4.

* * * * *